(12) United States Patent
Sharma et al.

(10) Patent No.: US 12,616,481 B2
(45) Date of Patent: May 5, 2026

(54) REPOSITIONABLE OVER-THE-SCOPE CLIP

(71) Applicant: BOSTON SCIENTIFIC MEDICAL DEVICE LIMITED, Galway (IE)

(72) Inventors: Deepak Kumar Sharma, Muzaffarnagar (IN); Sharath Kumar G, Kanakapura (IN)

(73) Assignee: Boston Scientific Medical Device Limited, Galway (IE)

( * ) Notice: Subject to any disclaimer, the term of this patent is extended or adjusted under 35 U.S.C. 154(b) by 51 days.

(21) Appl. No.: 18/740,027

(22) Filed: Jun. 11, 2024

(65) Prior Publication Data

US 2025/0025183 A1     Jan. 23, 2025

Related U.S. Application Data

(60) Provisional application No. 63/514,650, filed on Jul. 20, 2023.

(51) Int. Cl.
| | |
|---|---|
| *A61B 17/122* | (2006.01) |
| *A61B 17/128* | (2006.01) |
| *A61B 17/00* | (2006.01) |

(52) U.S. Cl.
CPC ...... *A61B 17/1285* (2013.01); *A61B 2017/00367* (2013.01); *A61B 2017/00818* (2013.01)

(58) Field of Classification Search
CPC ............ A61B 17/12009; A61B 17/122; A61B 17/1227; A61B 17/128; A61B 17/1285; A61B 2017/00296; A61B 2017/00367; A61B 2017/00818; A61B 2017/1225
See application file for complete search history.

(56) References Cited

U.S. PATENT DOCUMENTS

2021/0396986 A1 * 12/2021 Mushtaque ........... G02B 5/005
2022/0071634 A1     3/2022 Erdman et al.

FOREIGN PATENT DOCUMENTS

| CN | 205107799 U | 3/2016 |
|---|---|---|
| CN | 109362440 A | 2/2019 |
| WO | 2006/014496 A2 | 2/2006 |

* cited by examiner

*Primary Examiner* — Majid Jamialahmadi
(74) *Attorney, Agent, or Firm* — Fay Kaplun & Marcin, LLP

(57) ABSTRACT

A system includes a cap having first and second cap members, a clip, and first and second coupling members. The clip includes a first part rotatably coupled to a second part and first members coupled to the first part and corresponding second members coupled to the second part. Each of the first members is coupled to a corresponding one of the second members to form an iris mechanism operating to alter a size of a central opening of the clip when the parts are rotated relative to one another between open/closed configurations. The first coupling member is coupled between the first cap member and the first part, and the second coupling member is coupled between the second cap member and the second part so that, upon rotation of the first cap member relative to the second cap member, the first part is rotated relative to the second part.

10 Claims, 10 Drawing Sheets

REPOSITIONABLE OVER-THE-SCOPE CLIP

PRIORITY CLAIM

The present disclosure claims priority to U.S. Provisional Patent Application Ser. No. 63/514,650 filed Jul. 20, 2023; the disclosure of which is incorporated herewith by reference.

FIELD

The present disclosure relates to endoscopic devices and, in particular, relates to an endoscopic clipping device for treating tissue along the gastrointestinal tract.

BACKGROUND

Some endoscopic procedures (such as the removal of larger lesions (cancerous and other); tunneling under the mucosal layer of the GI tract to treat issues below the mucosa; full thickness removal of tissue (cancerous and other); treatment of issues on other organs by passing outside of the GI Tract (Natural Orifice Transluminal Endoscopic Surgery aka NOTES®)); and endoscopic treatment/ repair of post-surgical issues (e.g., post-surgical leaks, breakdown of surgical staple lines and/or anastomotic leaks); may increase the risk, in certain cases, of, for example, intraabdominal hypertension and seeding of cancer cells. In addition, these procedures generally create tissue openings that need to be hemo-statically sealed.

SUMMARY

The present disclosure relates to a clipping system for treating tissue. The system includes a cap, a clip, a first coupling member and a second coupling member. The cap is configured to be mounted over a distal end of an insertion device. The cap extends from a proximal end to a distal end and includes a channel extending therethrough. The cap includes a first cap member and a second cap member. The first cap member is rotatable relative to the second cap member.

The clip includes a peripheral body with a first part rotatably coupled to a second part and a plurality of first flexible members coupled to the first part and a corresponding plurality of second flexible members that are coupled to the second part. Each of the first flexible members is coupled to a corresponding one of the second flexible members to form an iris mechanism operating to alter a size of a central opening of the clip when the first and second parts are rotated relative to one another from a fully open configuration in which the central opening is a maximum size configured to receive target tissue therein and a fully closed configuration in which the central opening is a minimum size configured to clip target tissue received therein.

The first coupling member is coupled between the first cap member and the first part of the clip. The second coupling member is coupled between the second cap member and the second part of the clip so that, upon rotation of the first cap member relative to the second cap member, the first part of the clip is rotated relative to the second part of the clip.

In an embodiment, the first cap member includes a helical feature and the second cap member includes a coupling arrangement engaging the helical feature so that linear movement of the first cap member relative to the second cap member rotates the first cap member relative to the second cap member.

In an embodiment, the helical feature is a groove and the coupling arrangement includes a projection extending from the second cap member to enter the groove of the first cap member.

In an embodiment, the system further includes a cap coupling arrangement configured to mount the cap on the insertion device. The first cap member is coupled to the cap coupling arrangement so that the first cap member can move longitudinally relative to the cap coupling arrangement, engagement between helical feature of the first cap member and the coupling of the second cap member translating longitudinal movement of the first cap member relative to the cap coupling arrangement into rotation of the second cap member relative to the first cap member.

In an embodiment, the first and second flexible members are configured to bias the iris mechanism toward the fully closed configuration.

In an embodiment, each of the first and second flexible members extends along a substantially circular arc.

In an embodiment, the first part of the clip is a first disc having a distal surface and wherein the second part of the clip is a second disc having a proximal surface adjacent to the distal surface of the first part.

In an embodiment, the first and second flexible members extend within a central space of the first and second discs, respectively.

In an embodiment, the system further includes a pull wire coupled to the first cap member so that movement of the pull wire relative to the cap coupling arrangement moves the first cap member longitudinally relative to the cap coupling arrangement.

In an embodiment, the iris mechanism is configured so that, when the first part of the clip is rotated relative to the second part of the clip in a direction reducing a distance between a point of connection between each first flexible member and the first part of the clip and a point of connection between the corresponding one of the second flexible members and the second part of the clip, the central opening of the iris mechanism is opened.

In addition, the present disclosure relates to a method of clipping tissue. The method includes coupling to an endoscope a device including a cap having a first cap member and a second cap member and a clip coupled to the cap via first and second control members, the clip including a first part rotatably coupled to a second part and a plurality of first flexible members extending within the first part, each of the first flexible members having a first end coupled to the first part, the clip further including a corresponding plurality of second flexible members each of which includes a first end coupled to the second part, a second end of each of the first flexible members being coupled to a second end of a corresponding one of the second flexible members to form an iris mechanism; rotating the first and second parts of the clip relative to one another in a first direction via the first and second control members to open a central opening of the clip to a fully open configuration in which the central opening is a maximum size configured to receive target tissue therein; drawing tissue through the central opening of the clip into the cap; and rotating the first and second parts of the clip relative to one another in a second direction opposite the first direction to close the clip to clip the tissue extending through the central opening of the clip.

In an embodiment, the device further includes a first coupling member coupled between the first cap member and the first part of the clip and a second coupling member coupled between the second cap member and the second part of the clip, further comprising rotating the first cap member relative to the second cap member to rotate the first part of the clip relative to the second part of the clip.

In an embodiment, the method further includes, after rotating the first and second parts of the clip relative to one another in the second direction to close the clip to clip the tissue extending through the central opening of the clip, withdrawing the endoscope and the cap proximally relative to the clip to a review position from which the clip and the clipped tissue are more clearly visible.

In an embodiment, the method further includes, after withdrawing the endoscope and the cap to the review position, advancing the endoscope and the cap distally toward the clip to either reopen and reposition the clip or finally deploy the clip.

In an embodiment, the clip is finally deployed by severing a connection between a control wire and the clip.

DETAILED DESCRIPTION

Figure 1A:
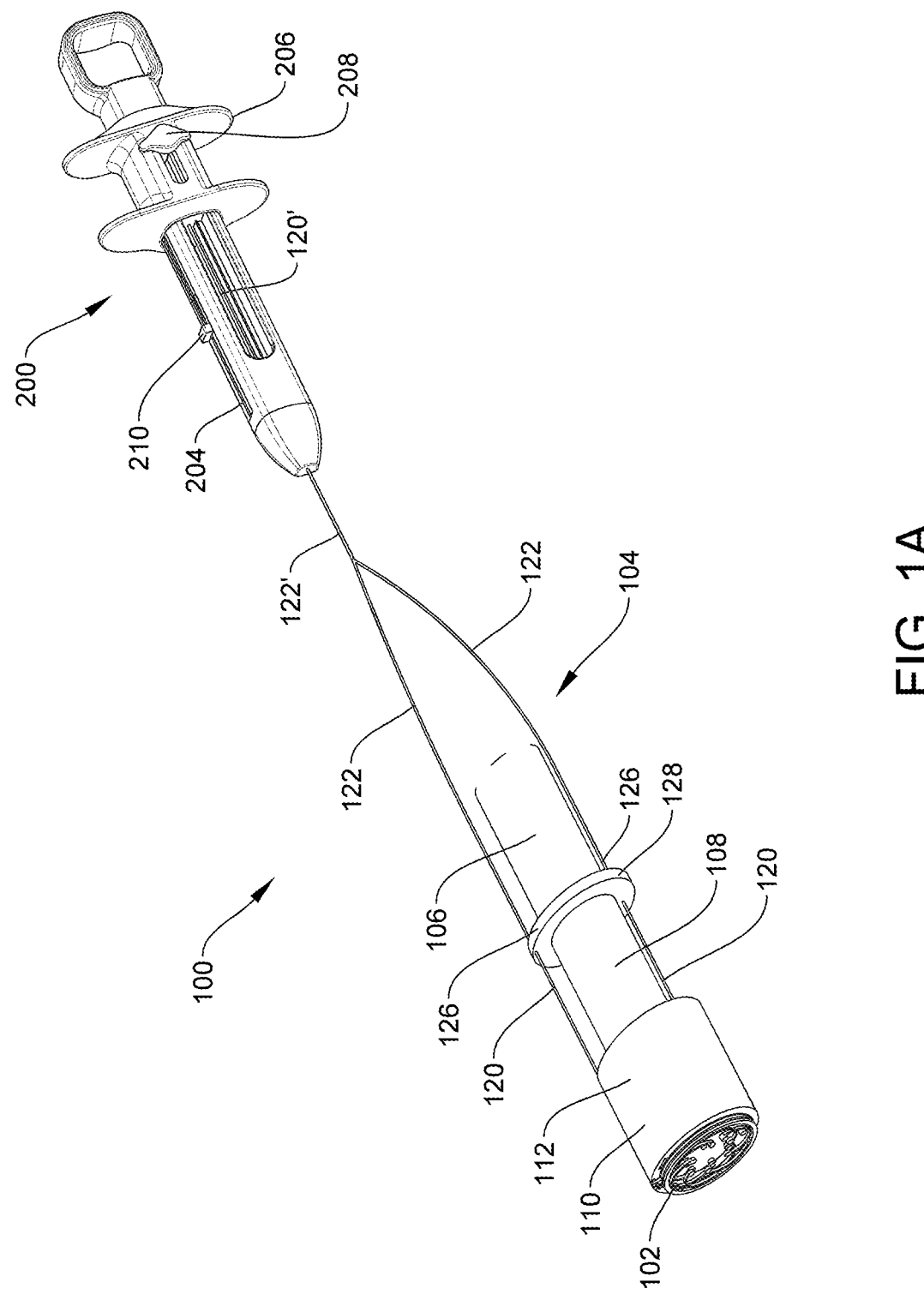
FIG. 1A shows a perspective view of a system according to an exemplary embodiment.

The present disclosure may be further understood with reference to the following description and the appended drawings, wherein like elements are referred to with the same reference numerals. The present disclosure relates to a clipping system and, in particular, relates to an over-the-scope endoscopic clipping system which may be used, for example, to close tissue openings created through a full thickness resection procedure within the GI tract while hygienically collecting tissue from the clipping site to minimize the potential for seeding of cancer or other undesirable tissues from the resection site to other areas of the body. Exemplary embodiments of the present disclosure comprise a disc-shaped clip configured to be mounted over a distal end of an endoscope via a cap coupled to the distal end of the endoscope. It should be noted that in this application the terms proximal and distal connote directions along the device toward (proximal) and away (distal) from a user.

The clip includes concentric discs each including a plurality of arced internal members that interact to form an iris mechanism opens and closes a central opening within the clip as the discs are rotated relative to one another. That is, as the discs of the clip are rotated relative to one another, the clip moves from a closed configuration in which a central opening formed between the points of the various arced members that are closest to the center of the disc is a minimum size (to clip tissue) and a fully open configuration in which the central opening is a maximum size (to permit target tissue to be drawn into the clip).

The system includes a cap configured to be mounted over the distal end of an insertion device (e.g., a flexible endoscope) and a plurality of control wires configured to permit a user to move the clip proximally and distally relative to a distal end of the cap and to rotate the discs of the clip between the fully open and closed configurations. The control wires of the disclosed embodiments also permit the user to separate the clip from the rest of the system when the user determines that the clip has been clipped to target tissue as desired.

The system also permits the user to move the insertion device away from a clip that has been clipped over a portion of tissue into a review configuration while maintaining a connection between the clip and the rest of the system. In the review configuration, the endoscope is drawn away from the clip to widen the field of view of the endoscopic vision system so that the user may review the position of the clip relative to target tissue (e.g., a tissue to be clipped). If, in the review configuration, it is determined that the clip is not clipped over the target tissue as desired, the clip may be re-opened so that the previously clipped tissue may be released and the cap and the clip may be repositioned relative to the target tissue to restart the clipping process. When the clip is again clipped over tissue and it is observed (e.g., in the review configuration) that the clip is clipped over the target tissue as desired, the clip is finally deployed by separating the clip from the control members.

It will be understood by those of skill in the art that exemplary embodiments of the present disclosure describe a clipping system which may be used to optimize a variety of tissue treatment/resection procedures within the body such as those, for example, performed using a flexible endoscope.

Figure 1B:
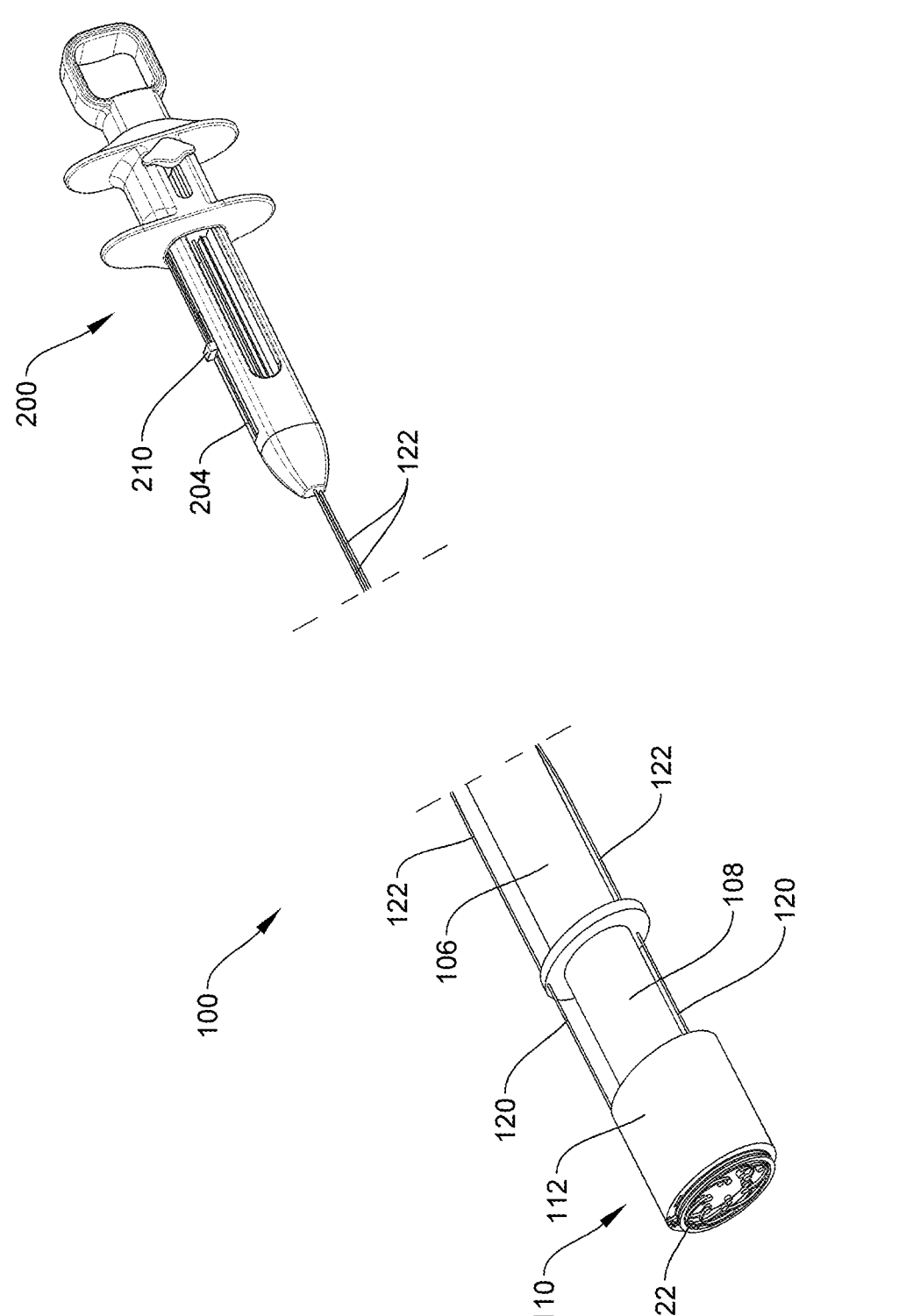
FIG. 1B shows a perspective view of a system according to an exemplary embodiment with an alternate handle.
Figure 1C:
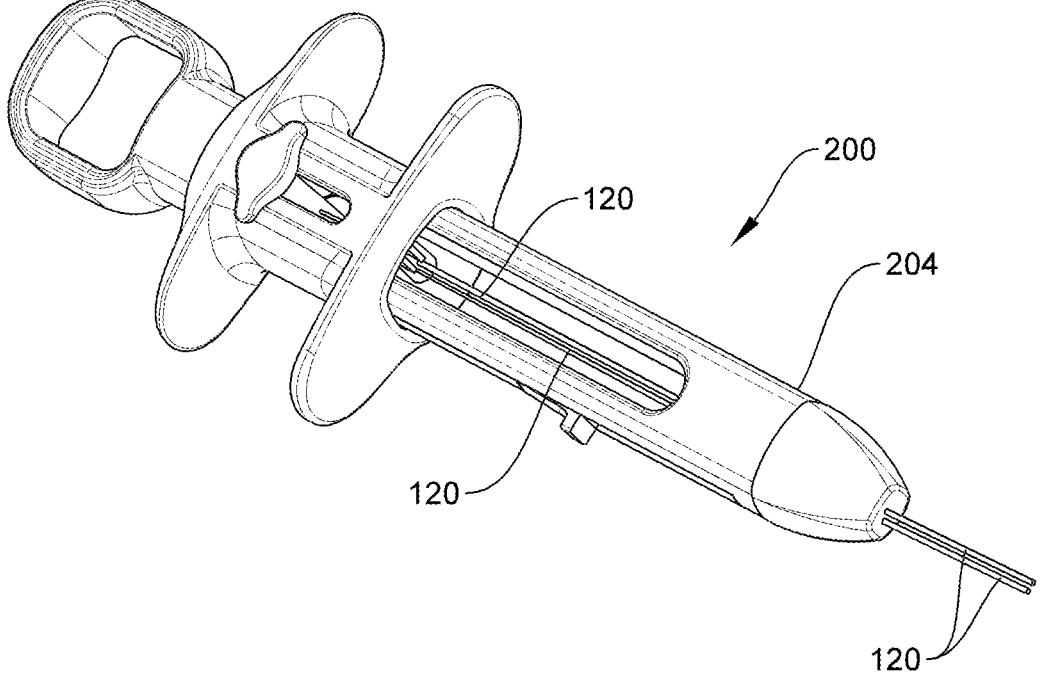
FIG. 1C shows a perspective view of the handle of FIG. 1B.

As shown in FIGS. 1A-7F, a clipping system 100 according to an exemplary embodiment of the present disclosure, comprises a clip 102 configured to be inserted through, for example, a body lumen to a target area to clip target tissue 10 (shown in FIG. 6)—e.g., a target portion of lesion to be clipped, edges of a wound or incision to be healed, etc. The clip 102 is insertable to the target area via an insertion device 104 including, for example, an endoscope 106 and a cap 110 mounted (e.g., via a friction fit) over a distal end 108 of the endoscope 106, as shown in FIG. 1. The cap 110 includes an outer body 112 and an inner body 114 rotatably mounted to one another. The clip 102 is configured to be positioned at a distal end of the cap 110 for insertion to a target site within a living body (e.g., adjacent to target tissue to be clipped) as the insertion device is navigated through a body lumen.

Those skilled in the art will understand that the cap 110 including the outer body 112 and the inner body 114 are, in this embodiment, formed of transparent material to permit the user to see as wide a field of view as possible via the vision system of the endoscope (mounted, e.g., on a distal end of the endoscope 106 which, when the cap 110 is mounted over the distal end of the endoscope 106, faces into an interior space of the inner body 114. The cap 110 of this embodiment is mounted over the endoscope 106, for example, so that the channel of the cap 110 is substantially longitudinally aligned with a longitudinal axis of the endoscope 106 to permit target tissue to be viewed through the channel of the cap 110 via the viewing system of the endoscope 106. In another embodiment, to enhance a visibility of the tissue and/or the clip 102, the cap 110 is formed of transparent material so that the user may see areas that would otherwise be blocked by the cap 110. Those skilled in the art will recognize that these components do not need to be transparent to function as described herein. This is generally preferred as it can enhance the user's ability to visualize the area surrounding the distal end of the endoscope, but is not necessary.

According to an exemplary embodiment, the clip 102 includes a distal disc 116 rotatably mounted to a proximal disc 118. The cap 110 including the outer body 112 and the inner body 114 of this embodiment are cylindrical to match the cylindrical profile of the endoscope 106. However, those skilled in the art will understand that the shapes of these items may be changed in any manner that does not impede the functioning of the system in placing and deploying the clip 102 as described below.

In this embodiment, the clip 102 is substantially circular (with each of the distal and proximal discs 116, 118, respectively being circular) so that the clip 102 may be made as large as possible without increasing a maximum cross-sectional extent of the system 100 beyond that of the circular distal end of the cap 110. Thus, in this embodiment, an outer diameter of the clip 102 is substantially the same as the outer diameter of the outer body 112. However, clips 102 of other shapes may be used depending on the characteristics of the target tissue, or of a tissue defect to be treated as would be understood by those skilled in the art.

The system 100 further includes at least one inner coil 120 that is slidably received within an outer coil 122. In each embodiment there are two inner coils 120 and two outer coils 122 with each of the inner coils 120 received within a corresponding one of the outer coils 120. In the embodiment of FIG. 1A, however, the two outer coils 122 (the corresponding inner coils 120) merge near a proximal end into a single combined outer coil 122' that houses a combined inner coil 120'. The combined inner coil 120 of FIG. 1A extends from a proximal end coupled to spool 206 that is slidably mounted on a body 204 of a handle 200. The combined inner coil 120' is coupled to each of the inner coils 120. A first one of the inner coils 120 extends to a distal end 124 coupled to the outer body 112 while the other inner coil 120 extends from the combined inner coil 120' to a distal end that is coupled to the inner body 114. The combined outer coil 122 is coupled to the body 204 of the handle and is coupled to the proximal ends of the outer coils 122. Each of the outer coils 122 extends (e.g., along an outer surface of the insertion device 104) to a distal end 126 coupled to flange 128 that, in use, is mounted in a fixed position on the insertion device 104. As will be described in more detail below, each of the inner coils 120 includes corresponding first and second control wires 140, 144 slidably received therein. In the embodiment of FIG. 1A, the first and second control wires 140, 144 from the inner coils 120 merge into a combined control wire at a location near where the inner coils 120 merge into the combined inner coil 120'. The combined control wire extends through the combined inner coil 120' to couple to a push button 208 that is slidably mounted on the spool 206.

The outer body 112 of this embodiment is coupled to the flange 128 so that the outer body 112 can move proximally and distally relative to the flange 128 but with the outer body 112 constrained to prevent relative rotation between the outer body 112 and the flange 128 (and consequently to the insertion device 104). The inner body 114 of this embodiment is mounted to the flange 128 so that a distance between the flange and the inner body 114 is fixed while the inner body 114 can rotate relative to the flange 128 and the outer body 112. Thus, as the user operates the spool 206 to move the inner coils 120 proximally and distally within the outer coils 122, the outer body 112 is moved proximally and distally over the inner body 114.

In the embodiment of FIG. 1B, the components and operation of the handle 200 are the same as that of the handle 200 of FIG. 1A except that the outer coils 122, the inner coils 120 and the first and second control wires 140, 144 do not merge into any combined coils or control wires. In this embodiment, the proximal ends of the outer coils 122 are coupled to the body 204 of the handle 200 and the proximal ends of the inner coils 120 are coupled to the spool 206 while the proximal ends of the first and second control wires 140, 144 are coupled to the push button 208. Each of the handles 200 of both FIG. 1A and FIG. 1B also includes a liner lock 210 that may be operated (as described below) to lock the spool 206 in place when it is desired to finally deploy the clip 102.

The inner body 114 of this embodiment is coupled to the outer body 112 via a pin 130 that projects outward from the inner body to ride slidably within a helical groove 132 formed on a radially inner surface of the outer body 112 (i.e., a surface of the outer body 112 that faces the inner body 114). Thus, as spool 206 is operated to move the inner coils 120 proximally and distally into and out of the outer coils 122, the outer body 112 is moved proximally and distally relative to the inner body 114 as the pin 130 rides in the groove 132 to rotate the inner body 114 relative to the outer body 112. Those skilled in the art will understand that in an alternative embodiment, the inner body 114 may be coupled to the flange 128 to permit proximal and distal motion of the inner body 114 relative to the flange 128 while rotation of the inner body 114 relative to flange 128 is prevented.

In this arrangement, the outer body 112 is mounted to the flange 128 in a manner that prevents movement of the outer body 112 proximally and distally relative to the flange 128 while rotation of the outer body 112 relative to the flange 128 is permitted. In addition, as would be understood by those skilled in the art, the same arrangement of the pin 130 and the groove 132 may be maintained or the arrangement of these elements may be reversed with the pin 130 extending radially inward from the outer body 112 to slidably reside in a groove 132 formed on a radially outer surface of the inner body 114.

In addition, any other known mechanism may be employed to convert longitudinal movement of one of the inner and outer bodies (114, 112, respectively) into rotation of the other of the inner and outer bodies (114, 112, respectively) without departing from the teachings of this application. Furthermore, as those skilled in the art will understand, the groove 132 may be replaced by a helical projection on one of the outer body 112 and the inner body 114 and the helical projection can be engaged by a projection or a plurality of projections extending from the other of the outer body 112 and the inner body 114.

The operation of the system 100 will be described in reference to the handle 200 of FIG. 1B. However, those skilled in the art will understand that the actions of the user are substantially the same with both handles 200. As indicated above, the first control wire 140 extends through a first one of the inner coils 120 from a proximal end coupled to the push button 208 to a distal end 142 coupled to the distal disc 116 of the clip 102. The inner coil 120 within which the first control wire 140 of this embodiment extends passes through the flange 128 and then passes through a lumen 113 extending through the outer body 112 from a proximal end to a distal end at which it exits the outer body 112. The first control wire 140 extends distally out of the inner coil 120 to couple to the distal disc 116. As the inner coil 120 within which the first control wire 140 extends is received within the lumen 113 of the outer body 112, this inner coil 120 and the first control wire 140 are prevented from rotating relative to the outer body 112.

The second control wire 144 extends within the other inner coil 120 from a proximal end coupled to the push button 208, through a lumen within the inner body 114 to a distal end 146 that is coupled to the proximal disc 118 of the clip 102. Thus, this inner coil 120 and the second control wire 144 are prevented from rotating relative to the inner body 114. As the first control wire 140 cannot rotate relative to the outer body 112 and the second control wire 144 cannot rotate relative to the inner body 114, rotation of the inner body 114 relative to the outer body 112 rotates the first and second control wires 140, 144 relative to one another. This, in turn, rotates the proximal and distal discs 118, 116 of the clip 102 (to which the first and second control wires 140, 144 are coupled) relative to one another to open and close the clip 102.

As can be seen in FIG. 1, the distal end 142 of the first control wire 140 is coupled to the distal disc 116 via a first projection 148 that extends radially outward from a radially outer-most edge of the distal disc 116. This permits the first control wire 140 to extend distally through a radially outer portion of the outer body 112 to engage the clip 102. The second control wire 144 is coupled to the proximal disc 118 via a second projection 150 that extends radially inward from a radially inner surface of the proximal disc 118 and the first and second projections 148, 150, respectively, are separated from one another about a circumference of the clip 102. The separation angle between the first and second projections may, for example, range from 10-180 degrees. Those skilled in the art will understand that the smaller this angle is, the more rotational stroke it provides to open the clip. In other words, if this angle is set at 10 degrees, the central opening of the clip 102 may be made larger as the projections can be moved through a rotation of 260 degrees (e.g., from the initial 10 degrees to a final position at 270 degrees) whereas an initial separation angle of 180 degrees permits only approximately 90 degrees of rotation (e.g., from the initial 180 degrees position to a final position at a separation of 270 degrees).

Figure 7A:
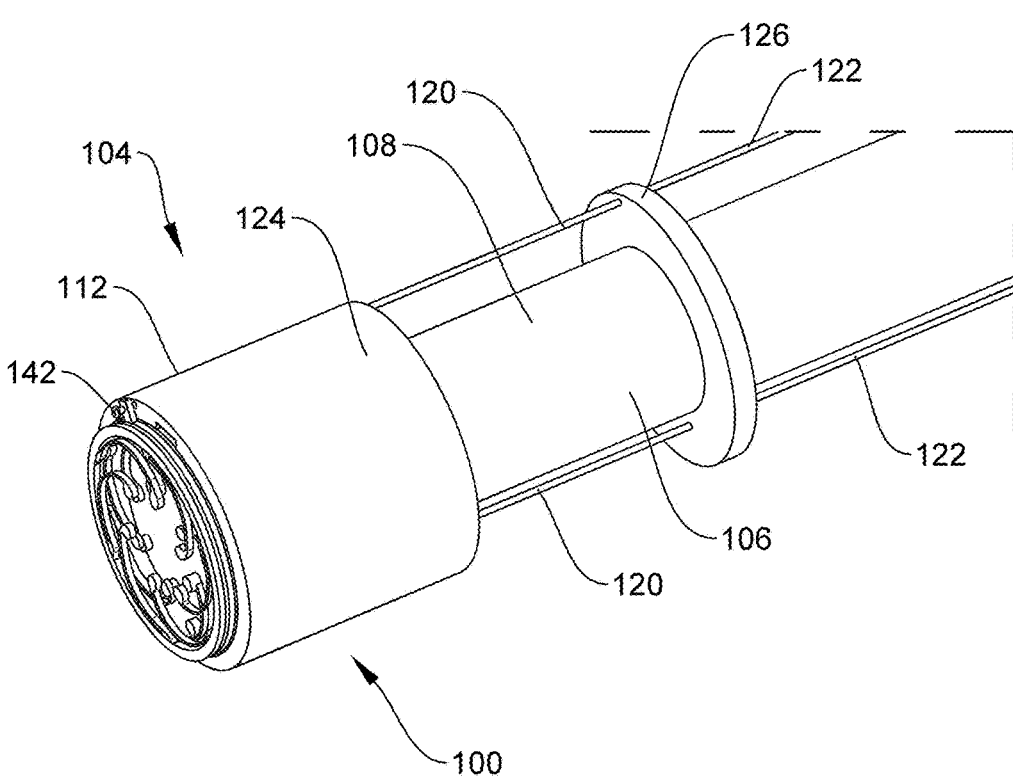
FIG. 7A shows the clip of FIG. 3 in an open configuration.
Figure 7B:
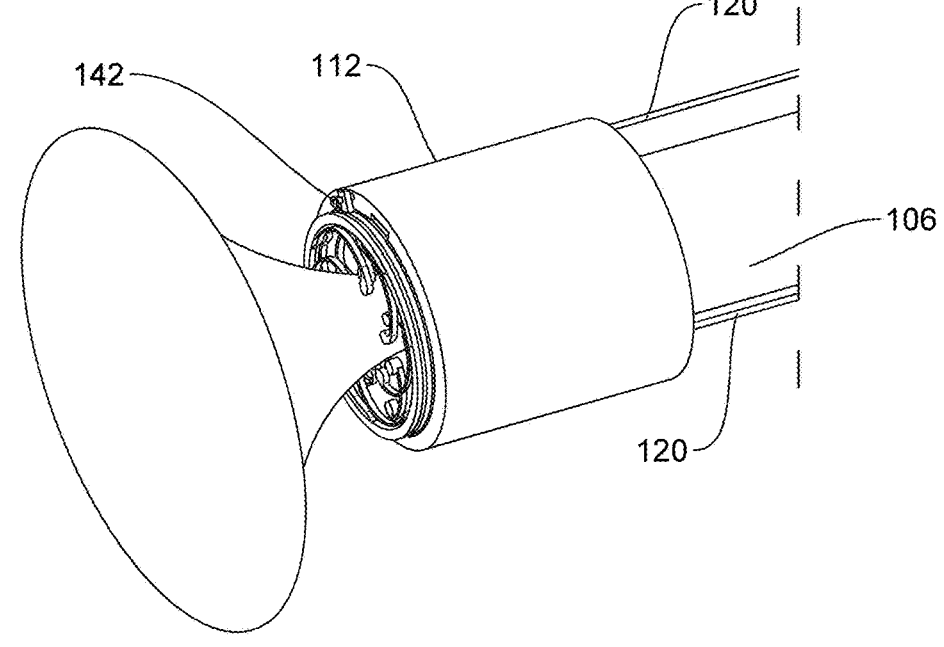
FIG. 7B shows the clip of FIG. 3 in an open configuration with tissue drawn into the clip.

Thus, when the inner body 114 rotates relative to the outer body 112 and the flange 128, the second control wire 144 rotates along with the inner body 114 relative to the outer body 112 and the first control wire 140. This, in turn, rotates the proximal disc 118 relative to the distal disc 116 to open and close the clip 102 as shown in FIG. 7A and as will be described in more detail below. Those skilled in the art will understand that, to apply the desired rotational forces to the proximal and distal discs 118, 116 against the natural bias of the clip (described in more detail below), the first and second control wires 140, 144, respectively, must have a sufficient degree of longitudinal stiffness. The first and second control wires of this embodiment are formed of hardened stainless steel. However, those skilled in the art will understand that Nitinol or any other suitable material may be employed.

The distal disc 116 of the clip 102 includes a plurality of flexible, first arced members 154 each of which extends into a central opening 155 of the distal disc 116 from a first end 156 attached to the distal disc 116 to a second end 158. The second end 158 of each of the first arced members 154 is coupled to a second end 162 of a corresponding flexible second arced member 160. In addition, the second end 158 of each of the first arced members 154 rests against an adjacent one of the first arced members 154. Each of the second arced members 160 extends from its second end 162 to a first end 164 that is attached to the proximal disc 118. Similarly, the second end 162 of each of the second arced members 160 rests against an adjacent one of the second arced members 160.

In this embodiment, when the clip 102 is in the closed configuration (i.e., when the second ends 158, 162 of the first and second arced members 154, 160 are at their radially inward-most position), each of the first arced members 154 extends along an arc that is substantially circular with the corresponding second arced member extending away from the second end 158 of its corresponding first arced member along an arc that is a continuation of the same circle. Those skilled in the art will understand that non-circular shapes may also be employed as desired with the size of the arc of any of the arced members depending on the diameter of the clip.

Figure 2:
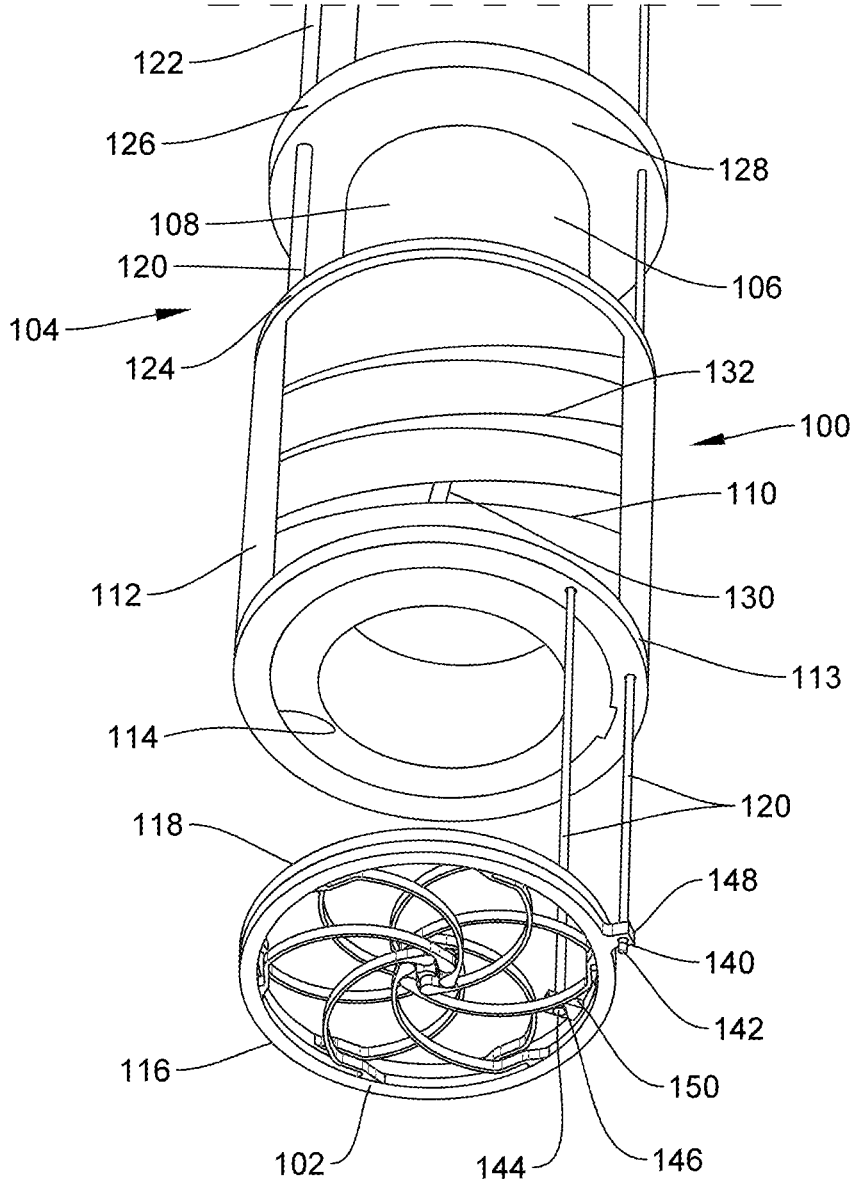
FIG. 2 shows a perspective view of a distal portion of a clipping system according to an exemplary embodiment of the present disclosure in an insertion configuration.
Figure 3:
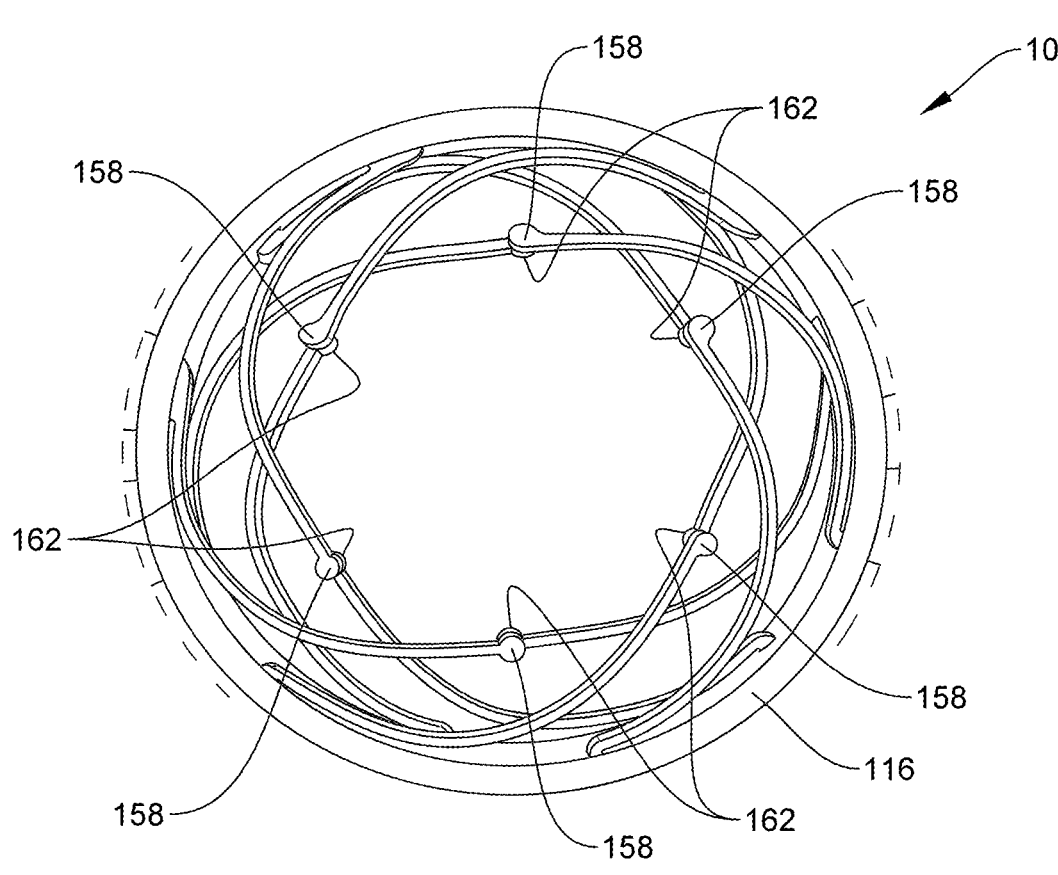
FIG. 3 shows a distal end of the clipping system of FIG. 1 with a clip in an open configuration.
Figure 5:
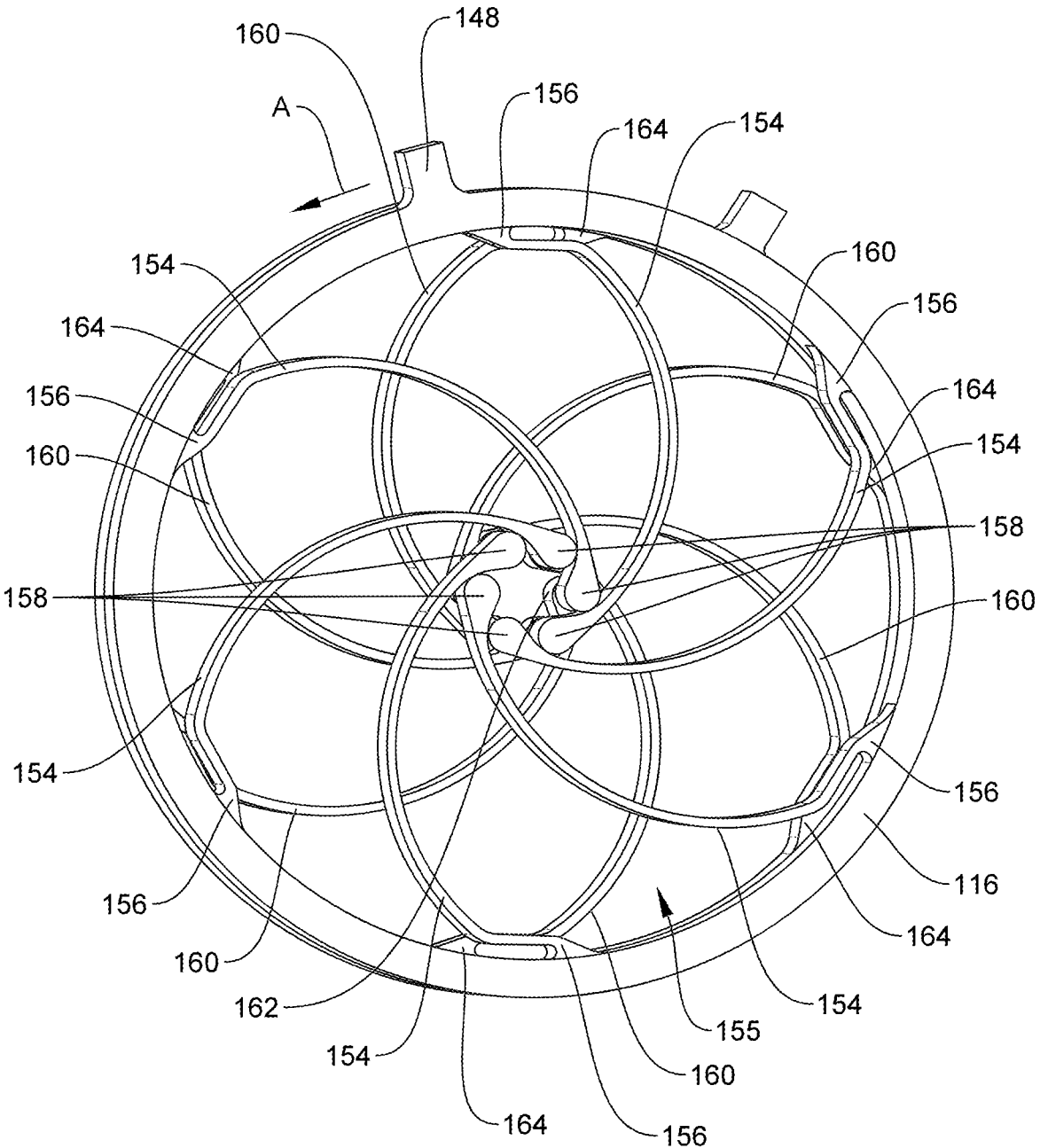
FIG. 5 shows a perspective view of the clip of FIG. 3.

Thus, when the proximal disc 118 is rotated relative to the distal disc 116 in the direction shown by the arrow A in FIG. 5, the first end 156 of each of the first arced members 154 is moved toward the first end 164 of its corresponding second arced member 160. This pushes all of the second ends 158, 162 radially outward toward the radially inner surfaces of the proximal and distal discs 118, 116, respectively, with each of the second ends 158, 162 pushing the second ends of the adjacent ones of the first and second arced members 154, 160 radially outward to enlarge the size of the central opening 155 as seen in FIG. 2. As would be understood by those skilled in the art, the spool 206 and the groove 132 are configured so that, when fully actuated, the amount of proximal-distal movement of the outer body 112 relative to the inner body 114, generates an amount of rotation of the proximal disc 118 relative to the distal disc 116 that will bring the clip 102 from a fully closed configuration (i.e., the central opening 155 is a minimum diameter) to a fully open configuration (the central opening 155 is at its greatest diameter).

If the spool 206 is then operated in the opposite direction and the proximal disc 118 is rotated relative to the distal disc 116 in a direction opposite the arrow A of FIG. 5, the clip 102 is moved away from the fully open configuration back toward the fully closed configuration. Furthermore, as would be understood by those skilled in the art, the first and second arced members 154, 160, respectively, are biased to urge the proximal disc 118 to rotate in a direction opposite the Arrow A so that the clip 102 is, when not acted on by an outside force, naturally returned to the fully closed configuration. The clip 102 of this embodiment is formed of a biocompatible plastic such as, for example, PEEK, Polypropylene, PU, PVC or PC.

Figure 4:
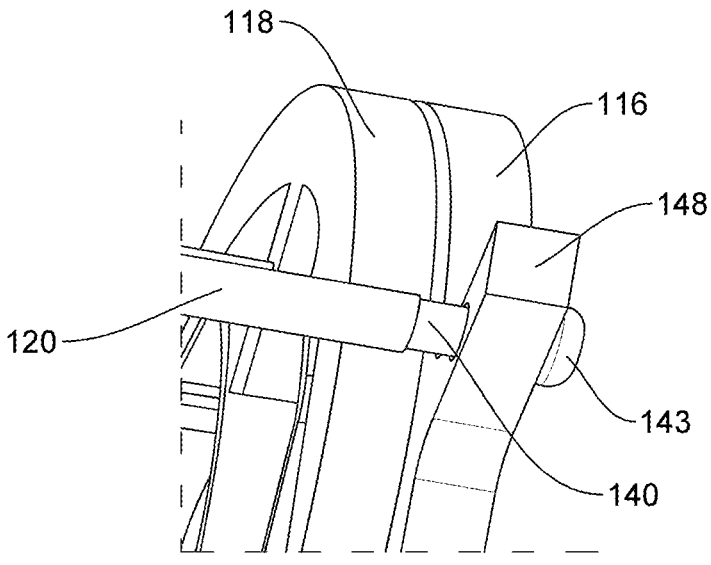
FIG. 4 shows a perspective view of a clip of the system of FIG. 1 showing a connection between the clip and a control wire.

As will be described in more detail below, the user may then open and close the clip 102 as often as desired by moving the spool 206 relative to the body 204 of the handle 200 in the desired direction to rotate the inner body 114 relative to the outer body 112 as desired (i.e., to achieve the rotation of the proximal disc 118 relative the distal disc 116 that corresponds to the opening or closing of the clip 102). In fact, the user may generally achieve closure of an open clip 102 by simply releasing the spool 206 so that the clip 102 returns to the fully closed configuration under its own natural bias. As seen in FIG. 4, the first control wire 140 extends through the inner coil 120 to extend through the first projection 148.

An enlarged end 143 at the distal end of the first control wire 140 prevents the first control wire 140 from being pulled proximally through the opening in the first projection 148. After a user has positioned a clip 102 as desired (e.g., after visually confirming that a target portion of tissue has been clipped by the clip 102 as desired), the user may finally deploy the clip 102 (see FIGS. 6 and 7F) by separating the clip 102 from the system 100. To do this, the user holds the distal end of the inner coil 120 against the proximal surface of the first projection 148 to prevent the inner coil 120 from moving proximally.

At the same time, the user applies proximal force to the first control wire 140 by sliding the push button 208 proximally relative to the spool 206 until a predetermined tension is applied to the first control wire 140 and the enlarged end 143 separates from the proximal portion of the first control wire 140. The actuation of the spool 206 and the push button 208 will simultaneously perform the same operation on the second control wire 144 (which, in this embodiment, has a substantially identical connection to the second projection 150) as the user's holding of the distal end of the other inner coil 120 in position against the proximal surface of the second projection 150 while moving the push button 208 proximally relative to the spool 206 applies the predetermined tension to the second control wire 144. When the enlarged ends of both the first and second control wires 140, 144, respectively, have been separated from the proximal portions thereof, the clip 102 is completely separated from the system 100 and remains closed, clipped over the target tissue under the force of its own natural bias.

Those skilled in the art will understand that, once the user has decided that the clip 102 is positioned as desired and the user wants to finally deploy the clip 102, the user may opt to use the liner lock 210 of the handle 200 to lock the spool 206 in position with the distal ends of the inner coils 120 abutting the proximal portions of the clip 102. This may facilitate operation of the push button 208 to fire the clip 102. In an alternative embodiment, the first and second control wires 140, 144 and the first and second projections 148, 150 may be configured so that when the predetermined tension is reached, the first and second projections 148, 150 fail releasing the first and second control wires 140, 144 intact from the clip 102.

In use, the flange 128 and the cap 110 (coupled to the inner coils 120, the first and second control wires 140, 144 and the clip 102) are mounted over the endoscope 106 (e.g., a flexible endoscope via, e.g., a friction fit) and the outer coils 122 (housing the inner coils 120 and the first and second control wires 140, 144) are extended along the length of the insertion device 104 and secured thereto if desired. The push button 208 is operated to move the first and second control wires 140, 144 proximally until the clip 102 drawn proximally into contact with the cap 110 and the spool 206 is operated to move the inner coils 120 so that the outer body 112 is moved relative to the inner body 114 to position the clip 102 in the closed position. The user then inserts the insertion device 104 including the system 100 mounted thereto into the patient's body (e.g., via a naturally occurring body orifice) and maneuvers the insertion device 104 through the body until the clip 102 is in a desired position relative to a portion of tissue to be clipped (e.g., through a natural body lumen).

The user then operates the spool 206 to move the clip 102 to the fully open configuration (FIG. 7A) and draws the target tissue through the central opening 155 of the clip 102 into an interior space of the cap 110 (FIG. 7B) (e.g., within an inner space defined by the inner body 114). As would be understood by those skilled in the art, the tissue may be drawn through the central opening 155 of the clip 102 by, for example, a grasper advanced into the cap 110 via a working channel of the endoscope that opens to an open interior space of the inner body 114 or by applying suction to the interior of the cap 110 through the application of negative pressure to the working channel of the endoscope 106.

Figure 7C:
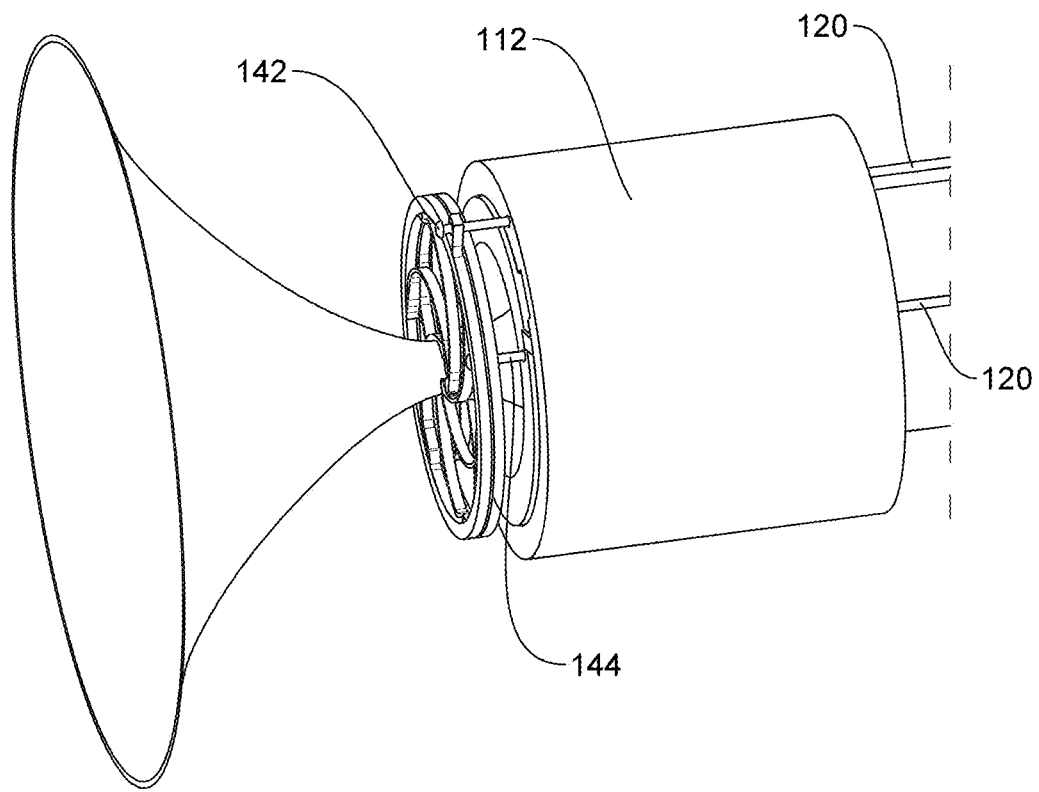
FIG. 7C shows the clip of FIG. 3 closed over the tissue drawn into the clip.
Figure 7D:
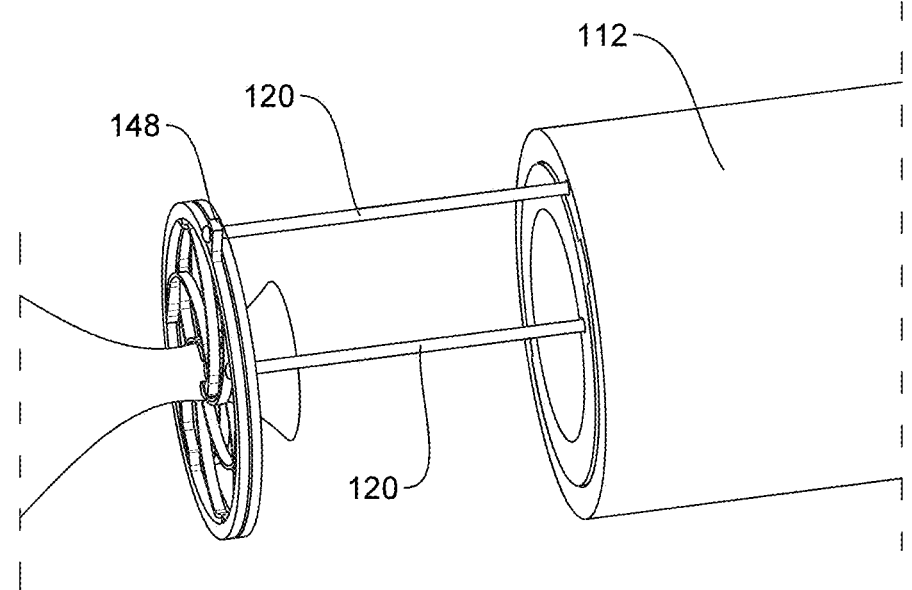
FIG. 7D shows the clip of FIG. 3 closed over target tissue and separated from the endoscope in a review configuration.

The user then operates the spool 206 to move the clip 102 to the fully closed configuration so that the natural bias of the first and second arced members 154, 160, respectively, constrict the central opening 155 around the target tissue (FIG. 7C). The user may then withdraw the endoscope 106 and the cap 110 proximally away from the clip 102 which remains in place clipped over the target tissue to a review configuration (FIG. 7D). To do this, the user moves the push button 208 distally relative to the spool 206 to advance the first and second control wires 140, 144, respectively, as the cap 110 is moved proximally so that the clip 102 remains coupled to the system 100 while the endoscope 106 and the cap 110 are separated therefrom. In this position, the user has a wider field of view and can better assess whether the clip 102 has been clipped over the target tissue as desired. If the user determines that the clip 102 is not positioned properly, the user advances the endoscope 106 distally while operating the push button 208 to withdraw the first and second control wires 140, 144 proximally so that the distal end of the cap 110 approaches the clip 102.

Figure 7E:
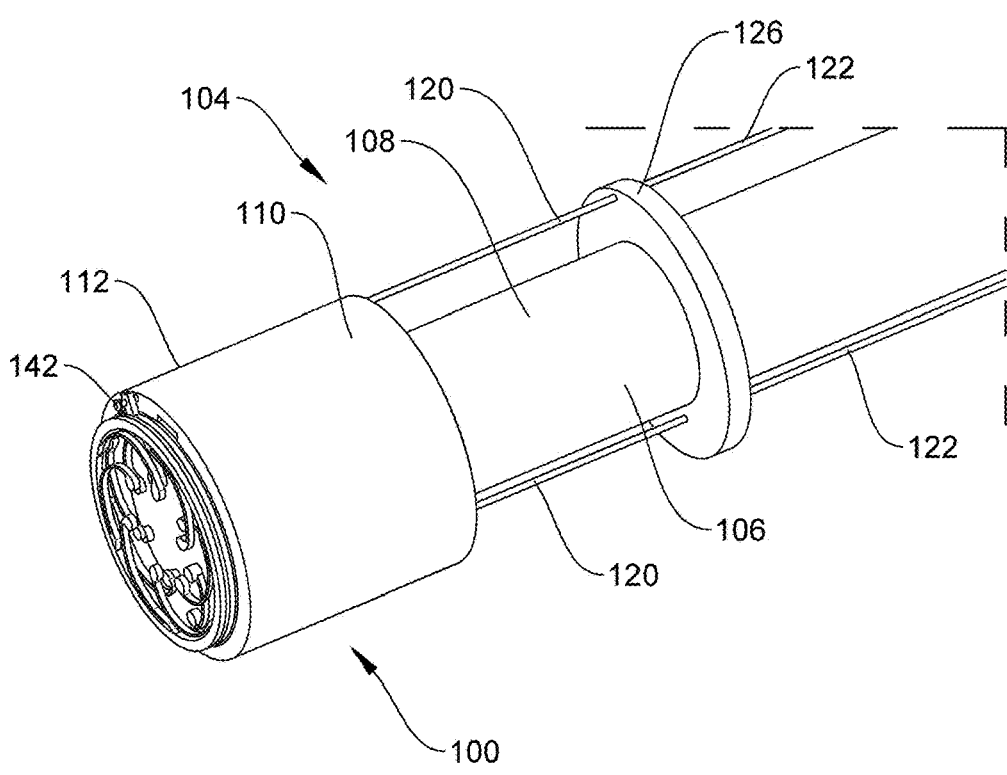
FIG. 7E shows the clip of FIG. 3 reopened and separated from the previously clipped tissue.

The user then operates the spool 206 to move the clip 102 back to the fully open configuration and pulls the endoscope 106 and the cap 110 proximally to separate the clip 102 from the previously clipped tissue (FIG. 7E). The user may then observe the target site and reposition the endoscope 106 and the cap 110 so that the clip 102 is positioned as desired in relation to the target tissue to be clipped. The user then draws a new portion of tissue through the central opening 155 in the same manner described above and operates the spool 206 to close the clip 102 over this new portion of target tissue.

The system may then be withdrawn to the review configuration so that the user can determine whether the clip 102 has been clipped over the target tissue as desired. This procedure may be repeated as many times as necessary until the user is satisfied with the placement of the clip 102. When the user determines that the clip 102 is clipped over target tissue as desired, the user advances the endoscope 106 distally by moving the push button 208 proximally over the spool 206 to draw the first and second control wires 140, 144 proximally into the inner coils 120 so that the distal end of the cap 110 approaches the clip 102. The user then advances the inner coils 120 distally until they abut against the proximal faces of the first and second projections 148, 150.

The user then draws the push button 208 proximally relative to the spool 206 to apply proximally directed force to the first and second control wires 140, 144 while maintaining the inner coils 120 position against the first and second projections 148, 150 until a predetermined tension is reached at which the enlarged ends of the first and second control wires 140, 144 separate from the proximal portions

Figure 6:
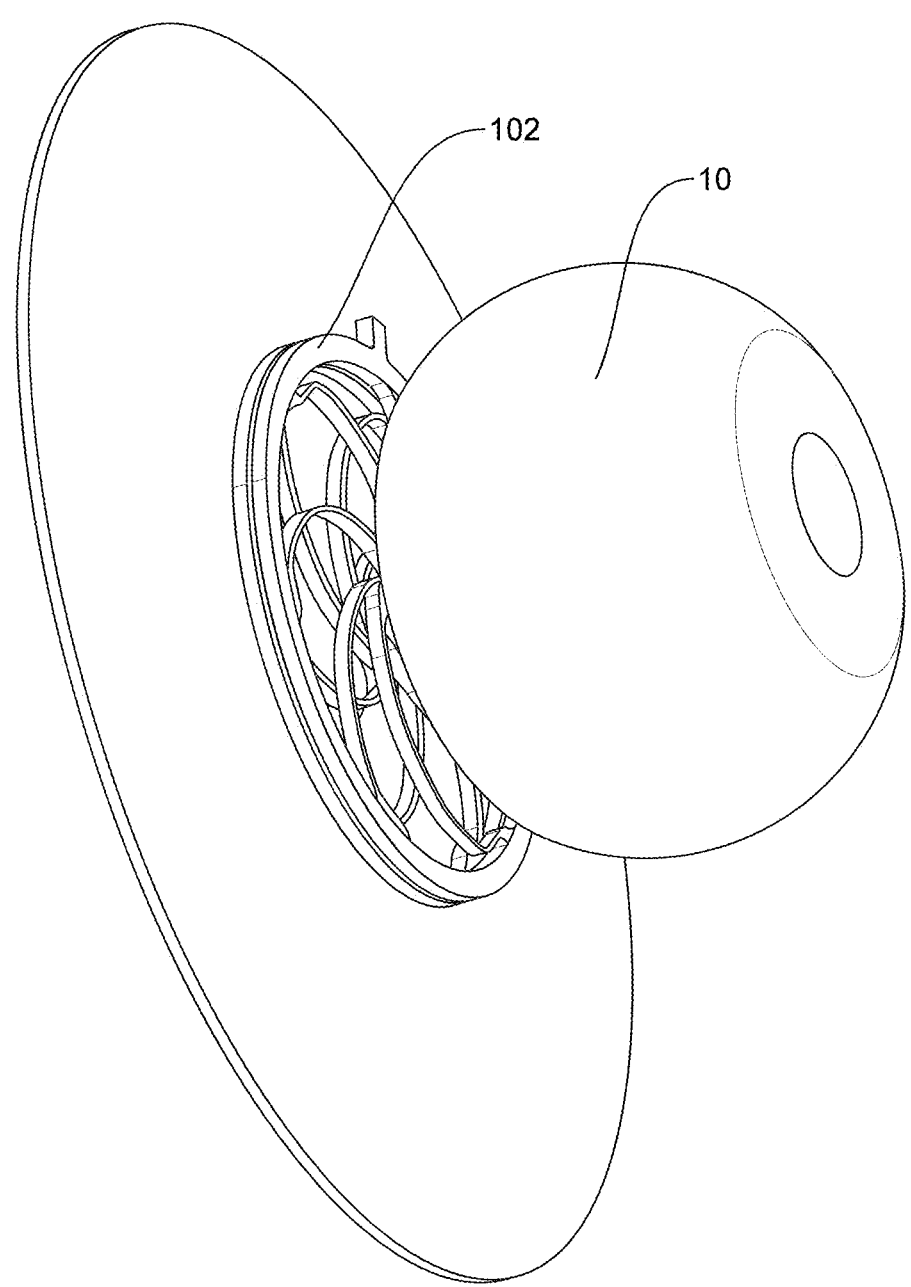
FIG. 6 shows a perspective view of the clip of FIG. 3 clipped over a portion of tissue separated from the clipping system in a finally deployed configuration.
Figure 7F:
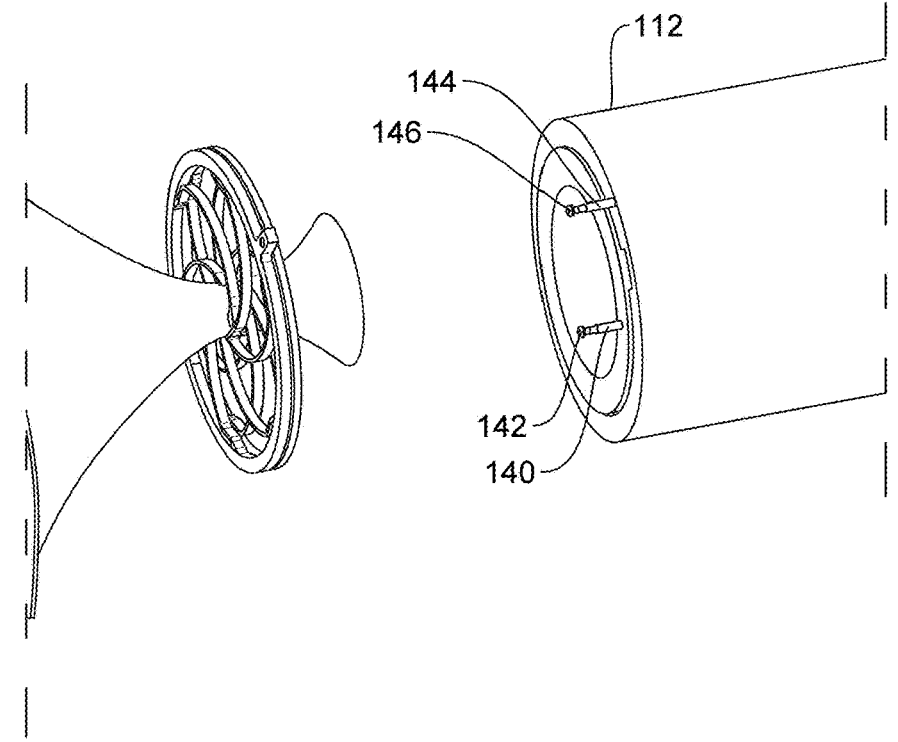
FIG. 7F shows the clip of FIG. 3 separated from the clipping system and finally deployed clipped over target tissue.

11 thereof. When the enlarged ends of both the first and second control wires 140, 144, respectively, have been separated from the proximal portions thereof, the clip 102 is completely separated from the system 100 and remains closed, clipped over the target tissue under the force of its own natural bias (FIGS. 6 and 7F).

As discussed above, the clip 102 may be mounted to the insertion device, which may include any standard endoscope 106. The clip 102 may be mounted to the endoscope 106 via the cap 110, which is sized, shaped and configured to be mounted over the distal end of the endoscope 106. As will be understood by those of skill in the art, the endoscope 106 is configured to be inserted through a body lumen to a target area within the lumen and thus, must be sufficiently flexible to navigate through even tortuous paths of the body lumen.

The cap 110 extends from a proximal end to a distal end and includes a channel extending therethrough (i.e., the proximal end of the cap 110 is open so that the vision system, working channel and other features of the distal end of the endoscope 106 open into the channel of the cap 110). In one embodiment, the cap 110 is substantially cylindrical. It will be understood by those of skill in the art, however, that the cap 110 may have any of a variety of shapes and configurations so long as the cap 110 is configured to be mounted over the distal end of the endoscope 106 and includes a channel sized and shaped to receive a target portion of tissue to be clipped.

It will be apparent to those skilled in the art that various modifications may be made in the present disclosure, without departing from the scope of the disclosure. Furthermore, those skilled in the art will understand that the features of any of the various embodiments may be combined in any manner that is not inconsistent with the description and/or the functionality of the embodiments.

What is claimed is:

1. A clipping system for treating tissue, comprising:
   a cap configured to be mounted over a distal end of an insertion device, the cap extending from a proximal end to a distal end and including a channel extending therethrough, the cap including a first cap member and a second cap member, wherein the first cap member is rotatable relative to the second cap member;
   a clip including a peripheral body including a first part rotatably coupled to a second part and a plurality of first flexible members coupled to the first part and a corresponding plurality of second flexible members that are coupled to the second part, each of the first flexible members being coupled to a corresponding one of the second flexible members to form an iris mechanism operating to alter a size of a central opening of the clip when the first and second parts are rotated relative to one another from a fully open configuration in which the central opening is a maximum size configured to receive target tissue therein and a fully closed configuration in which the central opening is a minimum size configured to clip target tissue received therein;

a first coupling member coupled between the first cap member and the first part of the clip; and
a second coupling member coupled between the second cap member and the second part of the clip so that, upon rotation of the first cap member relative to the second cap member, the first part of the clip is rotated relative to the second part of the clip.

2. The system of claim 1, wherein the first cap member includes a helical feature and the second cap member includes a coupling arrangement engaging the helical feature so that linear movement of the first cap member relative to the second cap member rotates the first cap member relative to the second cap member.

3. The system of claim 2, wherein the helical feature is a groove and the coupling arrangement includes a projection extending from the second cap member to enter the groove of the first cap member.

4. The system of claim 2, further comprising:
   a cap coupling arrangement configured to mount the cap on the insertion device,
   wherein the first cap member is coupled to the cap coupling arrangement so that the first cap member can move longitudinally relative to the cap coupling arrangement, engagement between helical feature of the first cap member and the coupling of the second cap member translating longitudinal movement of the first cap member relative to the cap coupling arrangement into rotation of the second cap member relative to the first cap member.

5. The system of claim 4, further comprising:
   a pull wire coupled to the first cap member so that movement of the pull wire relative to the cap coupling arrangement moves the first cap member longitudinally relative to the cap coupling arrangement.

6. The system of claim 1, wherein the first and second flexible members are configured to bias the iris mechanism toward the fully closed configuration.

7. The system of claim 6, wherein each of the first and second flexible members extends along a substantially circular arc.

8. The system of claim 6, wherein the first part of the clip is a first disc having a distal surface and wherein the second part of the clip is a second disc having a proximal surface adjacent to the distal surface of the first part.

9. The system of claim 8, wherein the first and second flexible members extend within a central space of the first and second discs, respectively.

10. The system of claim 1, wherein the iris mechanism is configured so that, when the first part of the clip is rotated relative to the second part of the clip in a direction reducing a distance between a point of connection between each first flexible member and the first part of the clip and a point of connection between the corresponding one of the second flexible members and the second part of the clip, the central opening of the iris mechanism is opened.

* * * * *